(12) United States Patent
Greenberg et al.

(10) Patent No.: US 8,231,637 B2
(45) Date of Patent: Jul. 31, 2012

(54) SURGICAL TOOL FOR ELECTRODE IMPLANTATION

(75) Inventors: Robert Greenberg, Los Angeles, CA (US); Da-Yu Chang, Rowland Heights, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 275 days.

(21) Appl. No.: 10/627,260

(22) Filed: Jul. 24, 2003

(65) Prior Publication Data

US 2007/0093852 A1   Apr. 26, 2007

(51) Int. Cl.
    *A61B 19/00* (2006.01)
(52) U.S. Cl. .......................................... 606/129
(58) Field of Classification Search .............. 607/53, 607/54, 141; 600/377; 606/129; 24/505, 24/518, 545, 546, 570
    See application file for complete search history.

(56) References Cited

U.S. PATENT DOCUMENTS

| | | | |
|---|---|---|---|
| 309,669 A * | 12/1884 | Wheatley ...................... 24/570 |
| 4,573,481 A | 3/1986 | Bullara |
| 4,628,933 A | 12/1986 | Michelson et al. |
| 4,925,073 A * | 5/1990 | Tarrson et al. .................. 225/44 |
| 4,969,468 A | 11/1990 | Byers et al. |
| 5,109,844 A | 5/1992 | De Juan, Jr. et al. |
| 5,215,088 A | 6/1993 | Normann et al. |
| 5,476,494 A | 12/1995 | Edell et al. |
| 5,507,807 A * | 4/1996 | Shippert ............................ 623/8 |
| 5,810,725 A | 9/1998 | Sugihara et al. |
| 5,935,155 A | 8/1999 | Humayan et al. |
| 5,941,250 A * | 8/1999 | Aramant et al. ............... 128/898 |
| 5,987,361 A | 11/1999 | Mortimer |
| 6,280,449 B1 * | 8/2001 | Blake ............................ 606/107 |
| 6,579,256 B2 * | 6/2003 | Hughes .......................... 604/60 |
| 6,697,677 B2 * | 2/2004 | Dahl et al. .................... 607/128 |
| 7,288,096 B2 * | 10/2007 | Chin .............................. 606/129 |
| 2002/0099420 A1 | 7/2002 | Chow et al. |

FOREIGN PATENT DOCUMENTS

EP    0460320 A1 * 11/1991
EP    0460320 A2    12/1991

OTHER PUBLICATIONS

U.S. Appl. No. 11/440,541, filed May 2006, Greenburg et al.*
Husain, M.D., Deeba, et al., Surgical Approaches to Retinal Prosthesis Implantation; pp. 105-111.

* cited by examiner

*Primary Examiner* — Gary Jackson
*Assistant Examiner* — Eric Blatt
(74) *Attorney, Agent, or Firm* — Scott B. Dunbar; Alessandro Steinfl

(57) ABSTRACT

The present invention is a surgical tool for implanting an electrode array and its connected cable within an orbital socket. The insertion tool is used to aid the surgeon in pulling the electrode wire and array through the scull, four-rectus muscles of the eye, and the sclera. The insertion tool consists of a medical grade ABS material that is commonly used in various medical products.

22 Claims, 7 Drawing Sheets

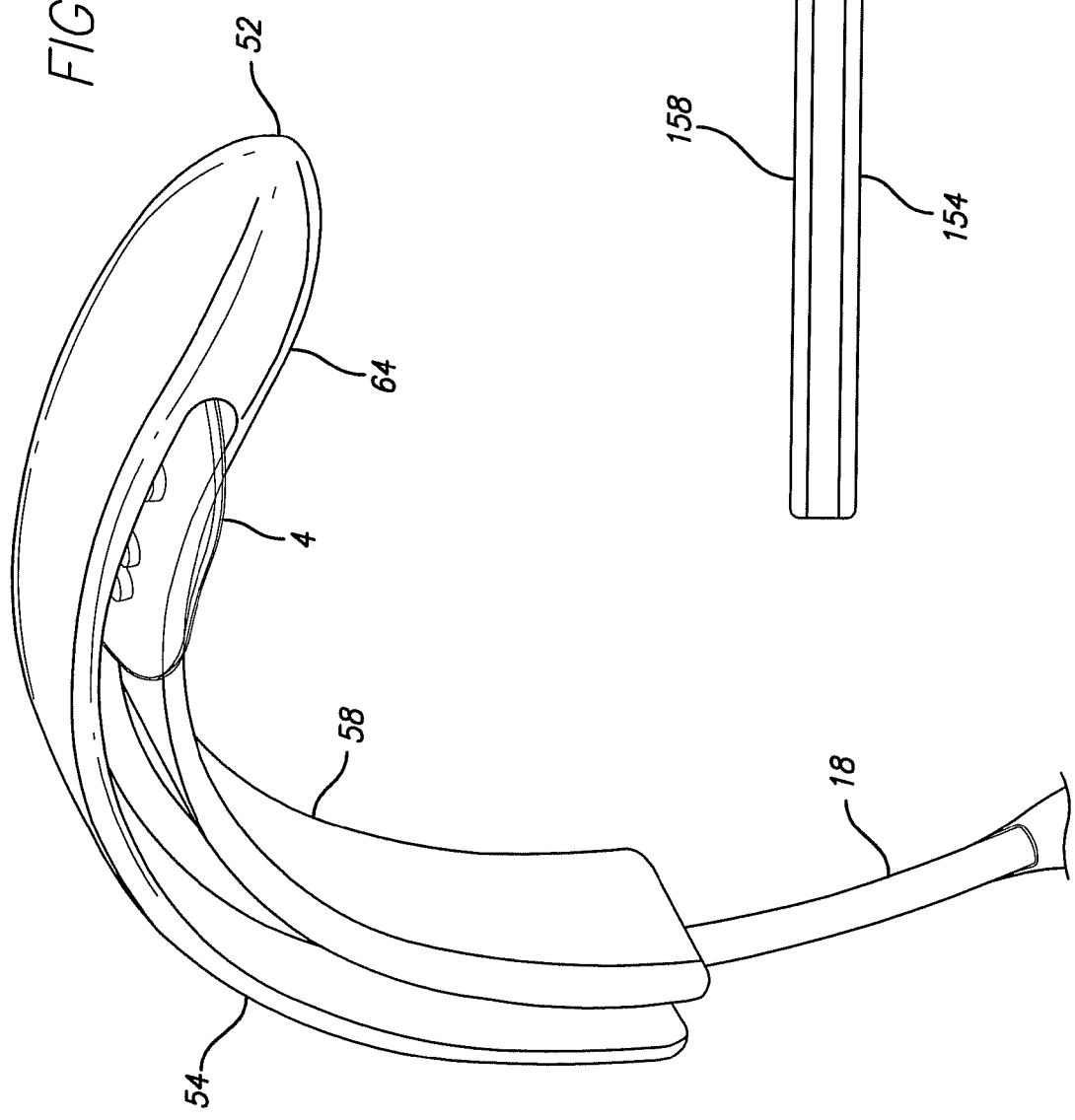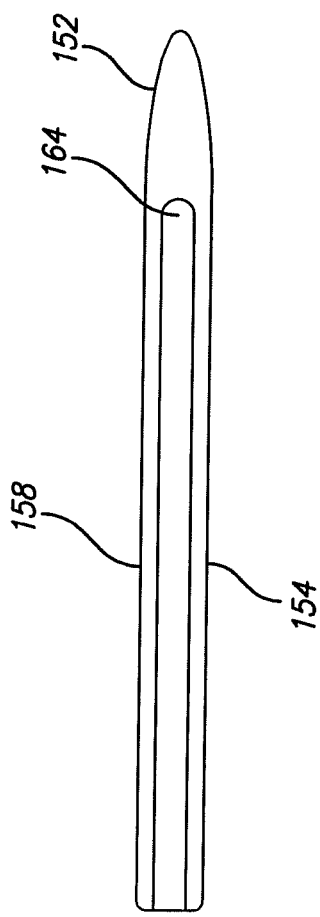

SURGICAL TOOL FOR ELECTRODE IMPLANTATION

FIELD OF THE INVENTION

The present invention is generally directed to implantable medical devices, in particular to a tool for implanting electrodes and their association wires.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concepts of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthesis devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across neuronal membranes, which can initiate neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface. This placement must be mechanically stable, minimize the distance between the device electrodes and the neurons, and avoid undue compression of the neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. Such a device increases the possibility of retinal trauma by the use of its "bed of nails" type electrodes that impinge directly on the retinal tissue.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina.

The retina is extraordinarily fragile. In particular, retinal neurons are extremely sensitive to pressure; they will die if even a modest intraocular pressure is maintained for a prolonged period of time. Glaucoma, which is one of the leading causes of blindness in the world, can result from a chronic increase of intraocular pressure of only 10 mm Hg. Furthermore, the retina, if it is perforated or pulled, will tend to separate from the underlying epithelium, which will eventually render it functionless. Thus attachment of a conventional prosthetic retinal electrode device carries with it the risk of damage to the retina, because of the pressure that such a device could exert on the retina.

Byers, et al. received U.S. Pat. No. 4,969,468 in 1990 which disclosed a "bed of nails" electrode array which in combination with processing circuitry amplifies and analyzes the signal received from the tissue and/or which generates signals which are sent to the target tissue. The penetrating electrodes are damaging to the delicate retinal tissue of a human eye and therefore are not applicable to enabling sight in the blind.

In 1992 U.S. Pat. No. 5,109,844 issued to de Juan et al. on a method of stimulating the retina to enable sight in the blind wherein a voltage stimulates electrodes that are in close proximity to the retinal ganglion cells. A planar ganglion cell-stimulating electrode is positioned on or above the retinal basement membrane to enable transmission of sight-creating stimuli to the retina. The electrode is a flat array containing 64-electrodes.

Norman, et al. received U.S. Pat. No. 5,215,088 in 1993 on a three-dimensional electrode device as a cortical implant for vision prosthesis. The device contains perhaps a hundred small pillars each of which penetrates the visual cortex in order to interface with neurons more effectively. The array is strong and rigid and may be made of glass and a semiconductor material.

U.S. Pat. No. 5,476,494, issued to Edell, et al. in 1995, describes a retinal array held gently against the retina by a cantilever, where the cantilever is anchored some distance from the array. Thus the anchor point is removed from the area served by the array. This cantilever configuration introduces complexity and it is very difficult to control the restoring force of the cantilever due to varying eye sizes.

Sugihara, et al. received U.S. Pat. No. 5,810,725 in 1998 on a planar electrode to enable stimulation and recording of nerve cells. The electrode is made of a rigid glass substrate. The lead wires which contact the electrodes are indium tin oxide covered with a conducting metal and coated with platinum containing metal. The electrodes are indium tin oxide or a highly electrically conductive metal. Several lead-wire insulating materials are disclosed including resins.

U.S. Pat. No. 5,935,155, issued to Humayun, et al. in 1999, describes a visual prosthesis and method of using it. The Humayun patent includes a camera, signal processing electronics and a retinal electrode array. The retinal array is mounted inside the eye using tacks, magnets, or adhesives. Portions of the remaining parts may be mounted outside the eye. The Humayun patent describes attaching the array to the retina using retinal tacks and/or magnets. This patent does not address reduction of damage to the retina and surrounding tissue or problems caused by excessive pressure between the retinal electrode array and the retina.

Mortimer's U.S. Pat. No. 5,987,361 of 1999 disclosed a flexible metal foil structure containing a series of precisely positioned holes that in turn define electrodes for neural stimulation of nerves with cuff electrodes. Silicone rubber may be used as the polymeric base layer. This electrode is for going around nerve bundles and not for planar stimulation.

The retina is also very sensitive to heat. Implanting a retinal prosthesis fully within the eye may cause excessive heat buildup damaging the retina. It is, therefore, advantageous to implant an electrode array on the retina attached by a cable to heat producing electronics which are implanted somewhere outside the eye. If no electronics are implanted in the eye, it is necessary to run one wire for each electrode from the electronics package to the electrode array. These wires must be extremely thin. While grouping them together in a cable with a protective sheath provides some protection, the array and cable must be handled carefully to prevent damage to the electrode array or cable.

Published US patent application 2002/0099420, Chow et al. describes a surgical tool for implantation of a retinal electrode array. The Chow device is a tube which is placed into the eye and to the implant location. Then fluid flows though the tube pushing the electrode array into place.

SUMMARY OF THE INVENTION

The present invention is a surgical tool for implanting an electrode array and its connected cable within an eye. The insertion tool is used to aid the surgeon in pulling the electrode wire and array through the scull, four-rectus muscles of the eye, and the sclera. The insertion tool consists of a medical grade ABS material that is commonly used in various medical products.

The novel features of the invention are set forth with particularity in the appended claims. The invention will be best understood from the following description when read in conjunction with the accompanying drawings.

BRIEF DESCRIPTION OF THE DRAWINGS

FIG. 8 is a perspective view of the preferred insertion tool, for inserting the array of FIGS. 1-7, having an curved tongs and a spring base.

FIG. 9 is a mechanical drawing of an alternate embodiment of the insertion tool illustrated in FIG. 8 having straight tongs and a.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
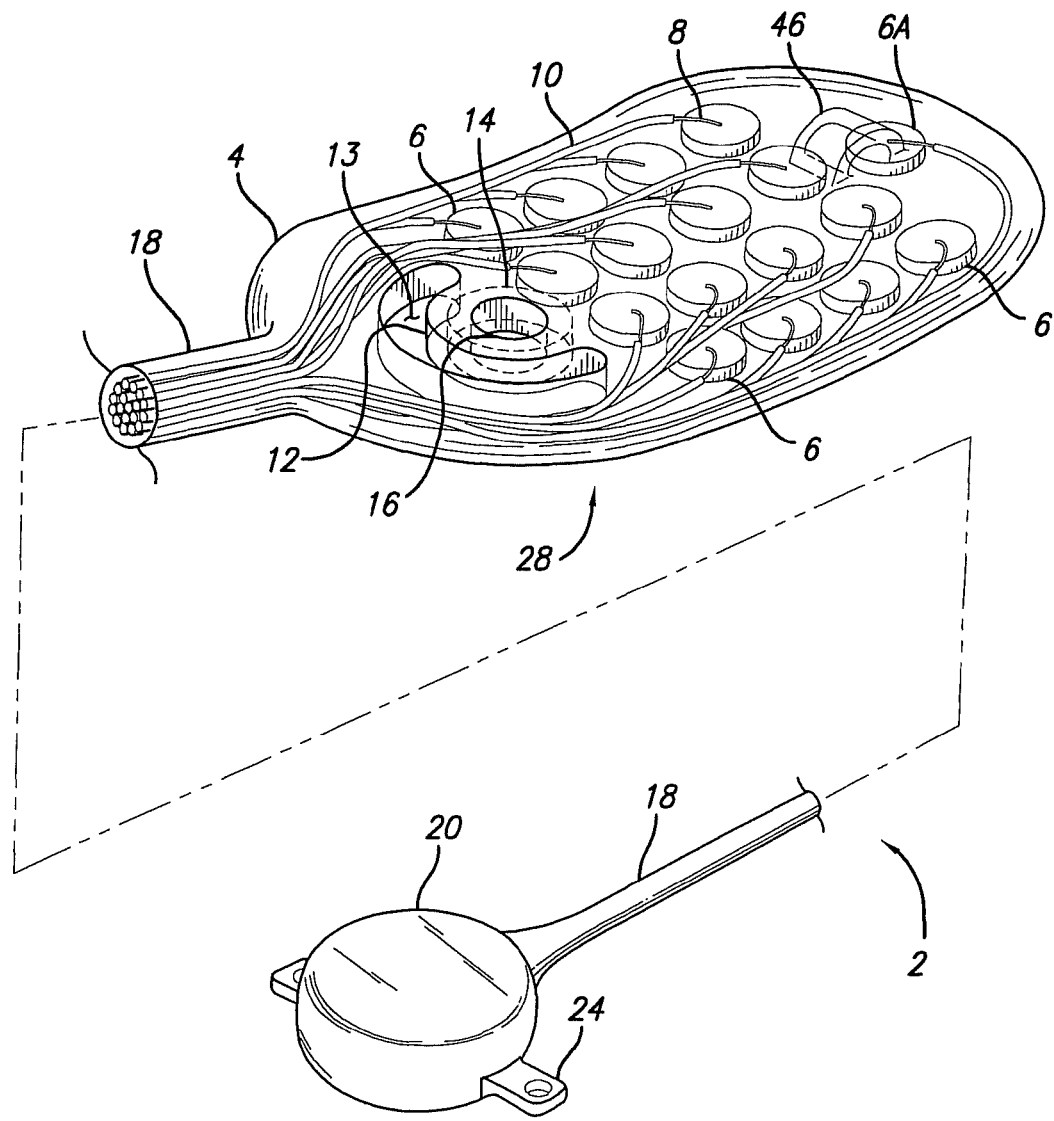
FIG. 1 is a perspective view of the retinal electrode array assembly showing the electrodes and signal conductors as well as mounting aperture for tacking the assembly inside the eye, wherein both the array and its associated electronics are located inside the eye.

FIG. 1 provides a perspective view of a preferred embodiment of the retinal electrode array (implanted by the surgical too of the resent invention), generally designated 2, comprising oval-shaped electrode array body 4, a plurality of electrodes 6 made of a conductive material, such as platinum or one of its alloys, but that can be made of any conductive biocompatible material such as iridium, iridium oxide or titanium nitride, and single reference electrode 6A made of the same material as electrode 6, wherein the electrodes are individually attached to separate conductors 8 made of a conductive material, such as platinum or one of its alloys, but which could be made of any biocompatible conductive material, that is enveloped within an insulating sheath 10, that is preferably silicone, that carries an electrical signal to each of the electrodes 6. "Oval-shaped" electrode array body means that the body may approximate either a square or a rectangle shape, but where the corners are rounded. The reference electrode 6A is not necessarily stimulated, but is attached to a conductor, as are electrodes 6. The electrodes could be used in another application as sensors to transmit electrical signals from a nerve. The electrodes 6 transmit an electrical signal to the eye while reference electrode 6A may be used as a ground, reference, or control voltage.

Electrode array body 4 is made of a soft material that is compatible with the body. In a preferred embodiment array body 4 is made of silicone having a hardness of about 50 or less on the Shore A scale as measured with a durometer. In an alternate embodiment the hardness is about 25 or less on the Shore A scale as measured with a durometer. It is a substantial goal to have electrode array body 4 in intimate contact with the retina of the eye.

Strain relief internal tab 12, defined by a strain relief slot 13 that passes through the array body 4, contains a mounting aperture 16 for fixation of the electrode array body 4 to the retina of the eye by use of a surgical tack, although alternate means of attachment such as glue or magnets may be used. Reinforcing ring 14 is colored and opaque to facilitate locating mounting aperture 16 during surgery and may be made of tougher material, such as high toughness silicone, than the body of the electrode array body to guard against tearing.

Signal conductors 8 are located in an insulated flexible feeder cable 18 carrying electrical impulses from the electronics 20 to the electrodes 6, although the electrodes can be sensors that carry a signal back to the electronics. Signal conductors 8 can be wires, as shown, or in an alternative embodiment, a thin electrically conductive film, such as platinum, deposited by sputtering or an alternative thin film deposition method. In a preferred embodiment, the entire retinal electrode array 2 including the feeder cable 18 and electronics 6 are all implanted inside the eye. Electronics 20 may be fixated inside the eye to the sclera by sutures or staples that pass through fixation tabs 24. The conductors are covered with silicone insulation.

Grasping handle 46 is located on the surface of electrode array body 4 to enable its placement by a surgeon using forceps or by placing a surgical tool into the hole formed by grasping handle 46. Grasping handle 46 avoids damage to the electrode body that might be caused by the surgeon grasping the electrode body directly. Grasping handle 46 also minimizes trauma and stress-related damage to the eye during surgical implantation by providing the surgeon a convenient method of manipulating electrode array body 4. Grasping handle 46 is made of silicone having a hardness of about 50 on the Shore A scale as measured with a durometer. A preferred embodiment of the electrode array body 4 is made of a very soft silicone having hardness of 50 or less on the Shore A scale as measured with a durometer. The reinforcing ring 14 is made of opaque silicone having a hardness of 50 on the Shore A scale as measured with a durometer.

Figure 2:
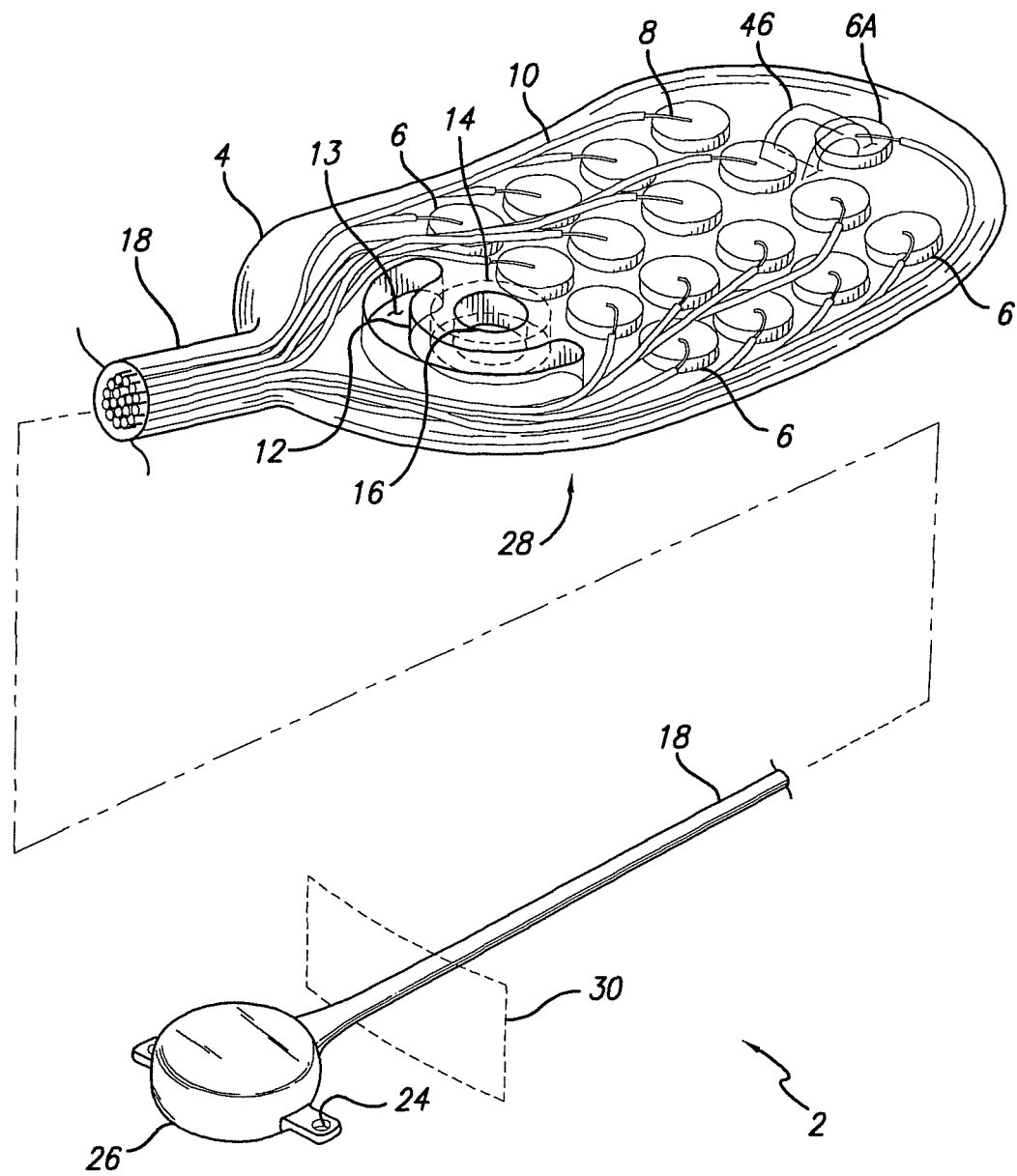
FIG. 2 is a perspective view of the retinal electrode array assembly showing the electrodes and signal conductors as well as mounting aperture for tacking the assembly inside the eye, wherein the associated electronics are located outside the eye.

FIG. 2 provides a perspective view of the retinal electrode array assembly 2 wherein the electrode array body 4 is implanted inside the eye and the electronics 20 are placed outside the eye with the feeder cable 18 passing through sclera 30. In this embodiment, electronics 38 are attached by fixation tabs 24 outside the eye to sclera 30.

Figure 3:
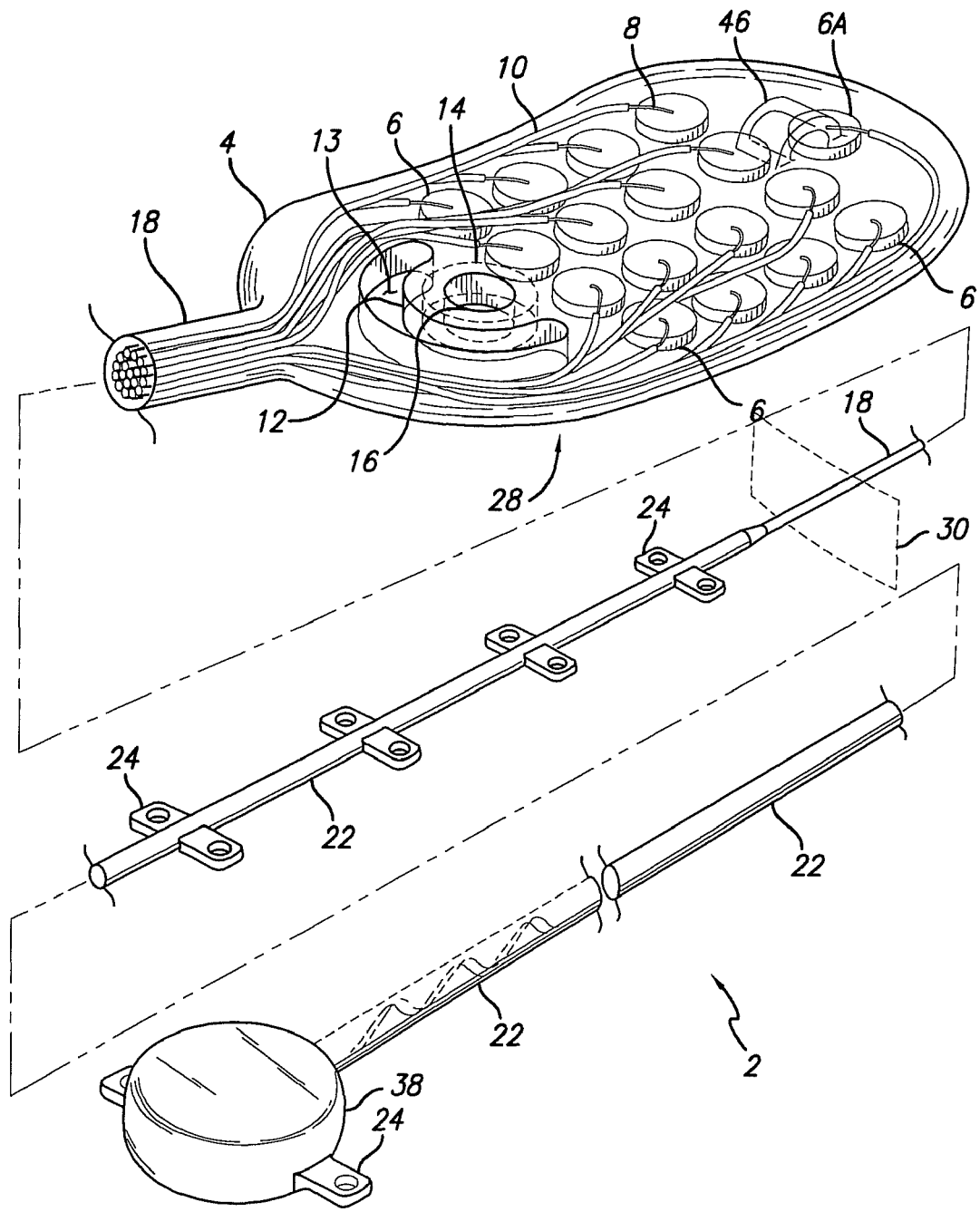
FIG. 3 is a perspective view of the retinal electrode array assembly wherein the array is installed inside the eye and the associated electronics are installed outside the eye at some distance from the sclera wherein the feeder cable contains both a coiled cable leading between the electronics and the sclera and a series of fixation tabs along the feeder cable for securing the feeder cable by suture.

FIG. 3 provides a perspective view of retinal electrode array 2 wherein electrode array body 4 is implanted on the retina inside the eye and electronics 38 are placed outside the eye some distance from sclera 30 wherein feeder cable 18 contains sheathed conductors 10 as silicone-filled coiled cable 22 for stress relief and flexibility between electronics 38 and electrode array body 4. Feeder cable 18 passes through sclera 30 and contains a series of fixation tabs 24 outside the eye and along feeder cable 18 for fixating cable 18 to sclera 30 or elsewhere on the recipient subject.

Figure 4:
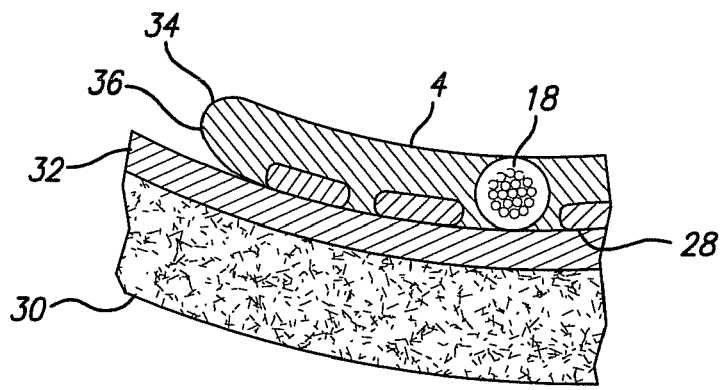
FIG. 4 is a cross-sectional view of the retinal electrode array, the sclera, the retina and the retinal electrode array showing the electrodes in contact with the retina.

FIG. 4 provides a cross-sectional view of electrode array body 4 in intimate contact with retina 32. The surface of electrode array body 4 in contact with retina 32 is a curved surface 28 substantially conforming to the spherical curvature of retina 32 to minimize stress concentrations therein. Further, the decreasing radius of spherical curvature of electrode array body 4 near its edge forms edge relief 36 that causes the edges of array body 4 to lift off the surface of retina 32 eliminating stress concentrations. The edge of electrode array body 4 has a rounded edge 34 eliminating stress and cutting of retina 32. The axis of feeder cable 18 is at right angles to the plane of this cross-sectional view. Feeder cable 18 is covered with silicone.

Figure 5:
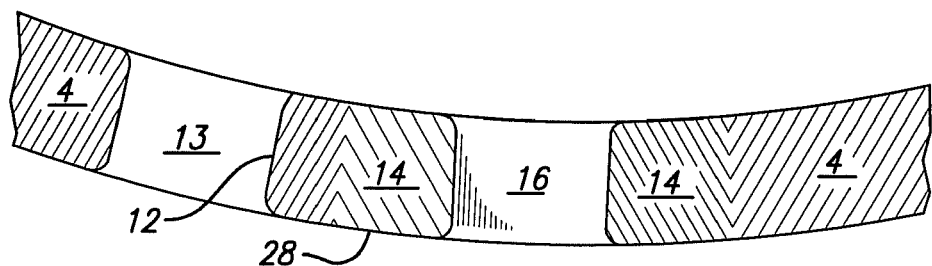
FIG. 5 depicts a cross-sectional view of the retinal electrode array showing a strain relief slot, strain relief internal tab and a mounting aperture through a reinforcing ring for a mounting tack to hold the array in position.

FIG. 5 provides a cross-sectional view of electrode array body 4 showing spherically curved surface 28, strain relief slot 13 and mounting aperture 16 through which a tack passes to hold array body 4 in intimate contact with the eye. Mounting aperture 16 is located in the center of reinforcing ring 14 that is opaque and colored differently from the remainder of array body 4, making mounting aperture 16 visible to the surgeon. Reinforcing ring 14 is made of a strong material such as tough silicone, which also resists tearing during and after surgery. Strain relief slot 13 forms strain relief internal tab 12 in which reinforcing ring 14 is located. Stresses that would otherwise arise in the eye from tacking array body 4 to the eye through mounting aperture 16 are relieved by virtue of the tack being located on strain relief internal tab 12.

Figure 6:
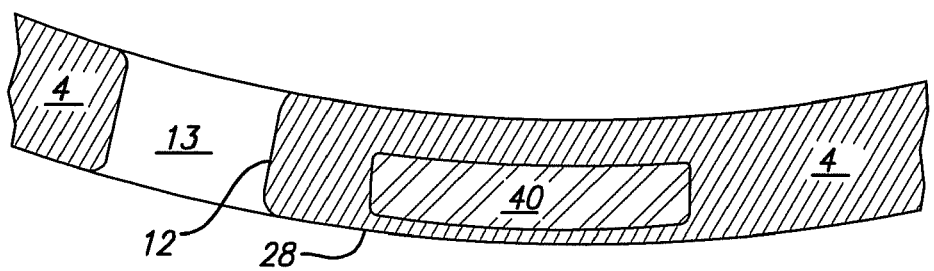
FIG. 6 illustrates a cross-sectional view of the retinal electrode array showing a strain relief slot and a ferromagnetic keeper to hold the array in position.

FIG. 6 provides a cross-sectional view of a preferred embodiment of electrode array body 4 showing ferromagnetic keeper 40 that holds electrode array body 4 in position against the retina by virtue of an attractive force between keeper 40 and a magnet located on and attached to the eye.

Figure 7:
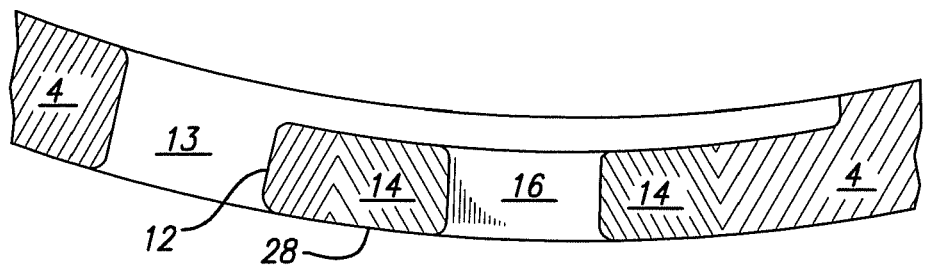
FIG. 7 illustrates a cross-sectional view of the retinal electrode array showing a strain relief slot and a mounting aperture through a reinforcing ring for a mounting tack to hold the array in position, wherein the strain relief internal tab containing the mounting aperture is thinner than the rest of the array.

FIG. 7 is a cross-sectional view of the electrode array body 4 wherein internal tab 12 is thinner than the rest of electrode array body 4, making this section more flexible and less likely to transmit attachment induced stresses to the retina. This embodiment allows greater pressure between array body 4 and the retina at the point of attachment, and a lesser pressure at other locations on array body 4, thus reducing stress concentrations and irritation and damage to the retina.

FIG. 8 is a perspective view of the preferred insertion tool 50. The electrode array body 4 and feeder cable 18 are extremely delicate. They must pass through a hole in the scull, pass under the four-rectus muscles of the eye, through the sclera and be attached to the retina. The insertion tool 50 has a rounded point 52 for gently separating muscle and flesh as the tool is passed through. The rounded point 52 is rigidly attached to a base 54 and top 56. Both the base 54 and the top 58 are rounded on the outside and square on the inside. The rounding helps the tool pass through flesh without causing damage. The electrode body 4 is place between the base 54 and top 58. Spring force traps the electrode array body 4 between the base 54 and top 58. The tool further includes a radius 64 between the base 54 and the top 58, which provides a space between the base 54 and the top 58 such that even pressure is applied along the length of the base 54 and the top 58. The radius 64 reduces stress concentrations that could crack the tool at the junction of the base and top with the base and top are deflected while loading or unloading the electrode array. The even pressure allows a surgeon to hold the electrode array body 4 and feeder cable 18 firmly without causing unnecessary stress on the electrode array body 4. The tool is fashioned from an inert biocompatible material that includes resilient elastic properties such ABS, stainless steel or titanium. ABS is suitable as a single use, disposable surgical tool while stainless steel or titanium could be steam sterilized and reused.

Once the electrode array body 4 and the feeder cable 18 are safely held in the surgical tool 50, the surgeon can pass the tool 50, electrode array body 4 and the feeder cable 18 in the same manner as a needle and thread. The preferred surgical tool 50 is curved to promote easy movement around the eye. The curvature of the tool generally conforms to the curvature of the outside of the sclera. Alternatively the surgical tool may be strait as shown in FIG. 9.

FIG. 9 shows an alternate embodiment of the surgical tool 150. The alternate surgical tool 150 has a strait base 54 and top 58, while retaining the radius 164 and rounded point 152 of the preferred embodiment. There are advantages to strait and curved surgical tools for much the same reasons there are advantages to strait and curved needles. Different surgeons may prefer different tools.

Figure 10:
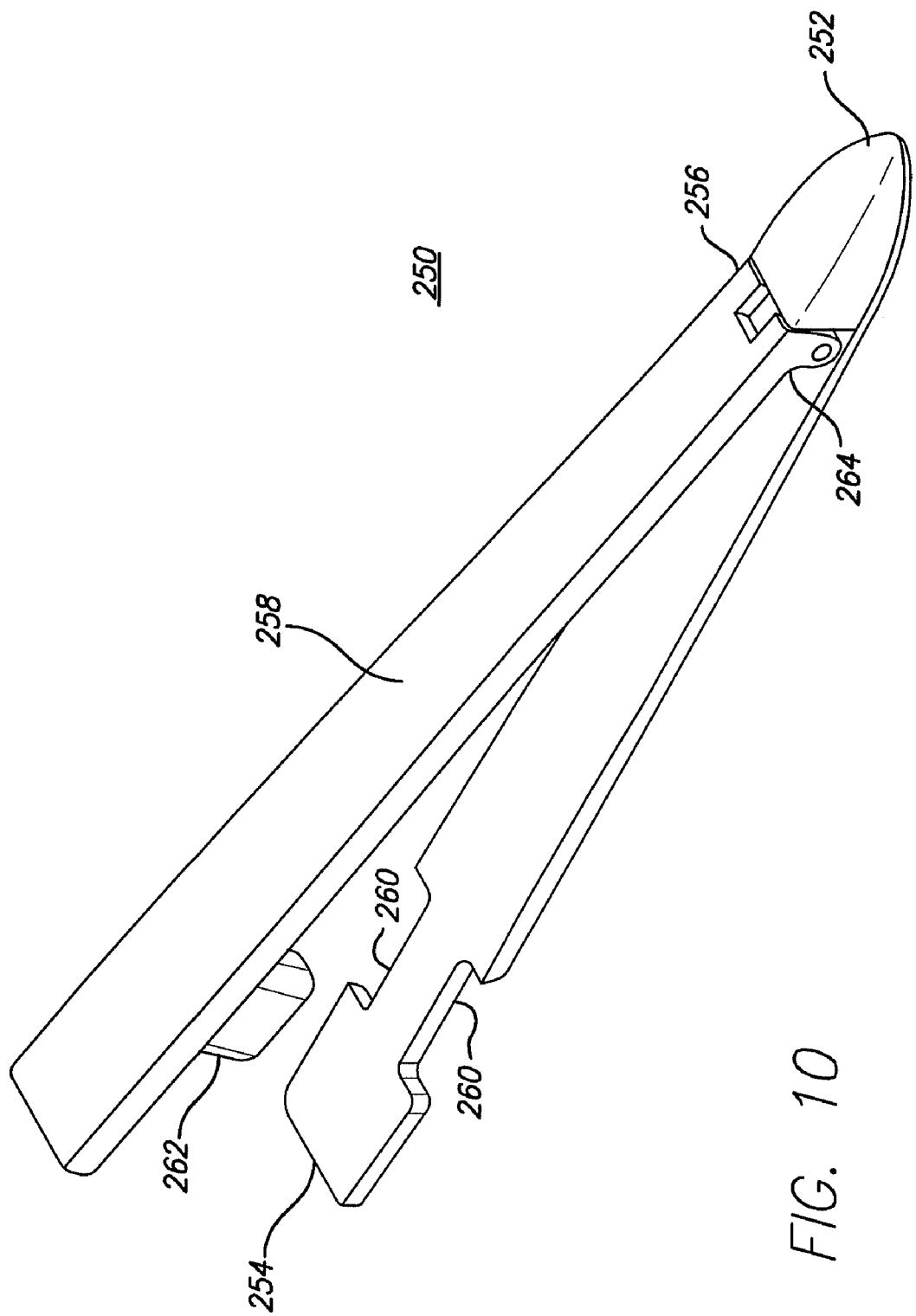
FIG. 10 is a perspective view of an alternate embodiment using a hinged base.

FIG. 10 shows another alternate embodiment. Rather than relying on spring force to hold the electrode array body 4 and the feeder cable 18 in the tool 250. The base 254 is rigidly attached to the rounded point 252, but the top 258 is attached by a hinge 256 to the base 254 and rounded point 252. This allows the surgeon more control of the force applied to the electrode array body 4 and the feeder cable 18. The hinge 256 further provides for easier loading and unloading of the electrode array. This embodiment retains the radius 264 to provide even pressure along the lengths of the base 254 and the top 258. This embodiment further includes notches 260 in the base 254, which mate with guides 262 in the top 258 to hold the electrode array body 4 and the feeder cable 18 in the tool 250, by holding the top 258 and base 254 together. The radius 264 reduces stress concentrations that could crack the tool at the junction of the base and top with the base and top are deflected while loading or unloading the electrode array.

Figure 11:
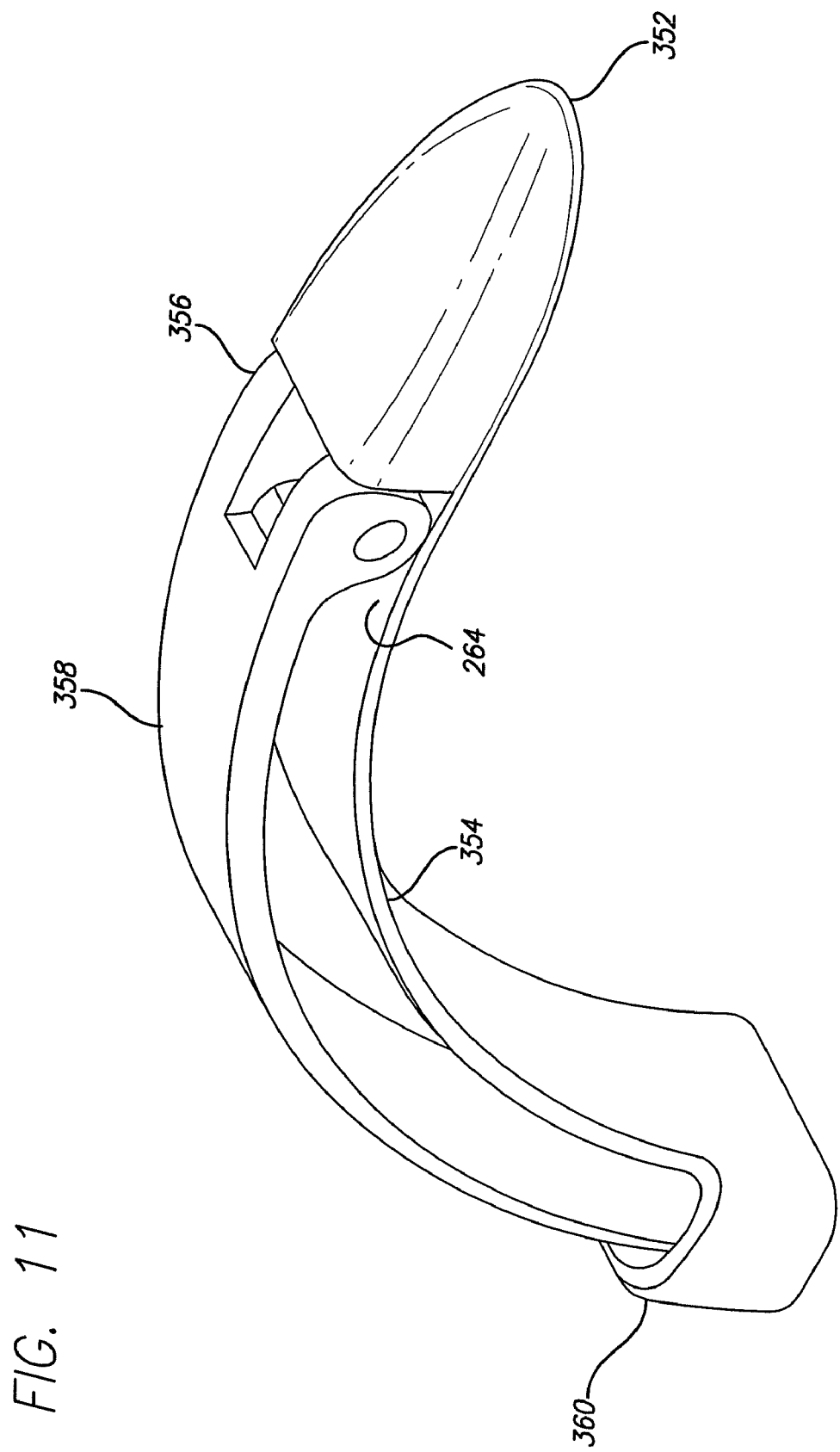
FIG. 11 is a perspective view of an alternate embodiment using curved tongs and a hinged base.

FIG. 11 shows another alternate embodiment, similar to that shown in FIG. 12. The base 354 is rigidly attached to the rounded point 352, but the top 358 is attached by a hinge 356 to the base 354 and rounded point 352. The hinge 356 further provides for easier loading and unloading of the electrode array. This embodiment retains the radius 264 to provide even pressure along the lengths of the base 354 and the top 358. However, the base 354 and top 358 are curved to allow for easier insertion of the tool. This embodiment further includes a keeper 360 attached to the base 354, which covers the top 358 to limit movement and prevents opening the tool and possibly dropping the array body 4.

While the invention has been described by means of specific embodiments and applications thereof, it is understood that numerous modifications and variations could be made thereto by those skilled in the art without departing from the spirit and scope of the invention.

We claim:

1. A surgical tool for implantation of an electrode array comprising:
    an electrode array;
    a rounded front exterior surface and a back interior surface opposite the rounded front exterior surface;
    a base portion coupled to the back interior surface of the end portion at a first location of the back interior surface; and
    a top portion coupled to the back interior surface of the end portion at a second location of the back interior surface;
    the open space suitable to receive and protect the between the first location and the second location defines an open space with a first opening towards an end opposite from said frontally closed end portion and a second opening lateral with respect to said top portion and said base portion during all operating conditions, the open space suitable to receive and protect an electrode array, the top portion and the base portion being movable with respect to each other to grip and hold the electrode array, between the base portion and the top portion, and
    wherein in at least one operating condition of the surgical tool the base portion is substantially parallel to the top portion.

2. The surgical tool according to claim 1, further comprising a hinge connecting said top portion to said end portion.

3. The surgical tool according to claim 1, wherein said top portion and based portion are curved to radii.

4. The surgical tool according to claim 3, wherein said radii approximate the radius of an eye.

5. The surgical tool according to claim 1, further comprising a keeper connected to said base portion and limiting travel of said top portion.

6. The surgical tool according to claim 1, further comprising notches in said base adapted to meet guides in said top portion and latch said base portion and said top portion together.

7. The surgical tool according to claim 1, fashioned from a biocompatible elastic material.

8. The surgical tool according to claim 7, wherein said biocompatible elastic material is ABS.

9. The surgical tool according to claim 7, wherein said biocompatible elastic material is stainless steel.

10. The surgical tool according to claim 1, wherein said open space between the base portion and the top portion is adapted to fit said electrode array when placed between said top portion and said base portion.

11. A method of implanting an electrode array comprising:
    providing a surgical tool having a frontally closed end portion having a curved shape, the curved shape defining a rounded front exterior surface and back interior surface opposite the rounded front exterior surface, a base portion coupled to the back interior surface of the end portion at a first location of the back interior surface, a top portion coupled to the back interior surface of the end portion at a second location of the back interior surface, wherein a distance between the first location and the second location defines an open space with a first opening towards an end opposite from the frontally closed end portion and a second opening lateral with respect to the base portion and the top portion, the top portion and the bottom portion being movable with respect to each other to grip and hold the electrode array, and wherein in at least one operating condition of the surgical tool the base portion is substantially parallel to the top portion;
    placing an electrode array inside said open space with a cable coupled to said electrode extending in a direction opposite from said end portion said opposite direction remaining open to accommodate said cable;
    passing said surgical tool and said electrode array into a body, said rounded-front surface first.

12. The method according to claim 11, further comprising the step of using said rounded-front surface to separate extra ocular muscle.

13. The method according to claim 11, further comprising the step of inserting said surgical tool into an orbital socket.

14. The method according to claim 11, further comprising the step of releasing said electrode array from said surgical tool once it is within the orbital socket.

15. The method according to claim 14, further comprising the step of inserting said surgical tool into the orbital socket through a hole in a skull.

16. The method according to claim 11, further comprising the step of providing a hinge between said top portion and said base portion.

17. The method according to claim 16, further comprising the step of applying pressure to said top portion and said base portion to retain said electrode array within said top portion and said base portion.

18. The method according to claim 11, further comprising the step of curving said top portion.

19. A surgical tool for implantation of an electrode array comprising:
- a frontally closed end portion having an exterior curved shape, the curved shape defining a rounded front surface and a back surface opposite the rounded front surface;
- a base portion coupled to the back surface of the end portion at a first location of the back surface, said base portion having an outer surface which is concave in one dimension and convex in another dimension, and having an inner surface which is convex in one dimension and flat in another dimension;
- a top portion coupled to the back surface of the end portion at a second location of the back surface, said top portion having an outer surface which is convex in two dimensions and having an inner surface which is concave in one dimension and flat in another dimension; and
- wherein a distance between the first location and the second location defines an open space with a first opening towards an end opposite from the frontally closed end portion and a second opening lateral with respect to the base portion and the top portion during all operating conditions to accommodate an electrical supply cable for said electrode array,
- wherein the base portion is substantially parallel to the top portion in at least one operating condition of the surgical tool.

20. The method according to claim 14, wherein releasing said electrode array from said surgical tool is performed through said lateral opening.

21. A surgical tool for implantation of an electrode array, the surgical tool comprising
- a frontally closed end portion having a curved shape, the curved shape defining a rounded front surface and a back surface opposite the rounded front surface;
- a base portion coupled to the back surface of the end portion at a first location of the back surface; and
- a top portion coupled to the back surface of the end portion at a second location of the back surface,
- the base portion and top portion defining an opening of the surgical tool lateral with respect to the base portion and top portion, wherein in a first operation condition a distance between the base portion and the top portion is controlled to allow retention of the electrode array and in a second operating condition the distance between the base portion and the top portion is controlled to allow release of the electrode array through the lateral opening.

22. The method according to claim 14, wherein said step of releasing is laterally releasing the electrode array through the open space.

* * * * *

UNITED STATES PATENT AND TRADEMARK OFFICE
CERTIFICATE OF CORRECTION

| | |
|---|---|
| PATENT NO. | : 8,231,637 B2 |
| APPLICATION NO. | : 10/627260 |
| DATED | : July 31, 2012 |
| INVENTOR(S) | : Robert Greenberg et al. |

It is certified that error appears in the above-identified patent and that said Letters Patent is hereby corrected as shown below:

In the Claims, Claim 1:

Col. 7, line 66, insert at the beginning of the line -- a frontally closed end portion having a curved shape, the curved shape defining --.

Col. 8, line 6, delete "the open space suitable to receive and protect" and replace with -- wherein a distance --.

Col. 8, line 12, delete "an" and replace with -- the --.

Signed and Sealed this
Thirtieth Day of April, 2013

Teresa Stanek Rea
*Acting Director of the United States Patent and Trademark Office*